(12) United States Patent
Kheraj

(10) Patent No.: US 11,311,638 B2
(45) Date of Patent: Apr. 26, 2022

(54) PORTABLE STERILIZATION CASE FOR PERSONAL PROTECTIVE EQUIPMENT

(71) Applicant: Reshma N Kheraj, Raleigh, NC (US)

(72) Inventor: Reshma N Kheraj, Raleigh, NC (US)

( * ) Notice: Subject to any disclaimer, the term of this patent is extended or adjusted under 35 U.S.C. 154(b) by 41 days.

(21) Appl. No.: 17/111,214

(22) Filed: Dec. 3, 2020

(65) Prior Publication Data

US 2021/0085813 A1    Mar. 25, 2021

Related U.S. Application Data

(60) Provisional application No. 62/994,041, filed on Mar. 24, 2020.

(51) Int. Cl.
*A61L 2/10* (2006.01)
*A61L 2/26* (2006.01)
*A61L 2/24* (2006.01)

(52) U.S. Cl.
CPC .............. *A61L 2/10* (2013.01); *A61L 2/24* (2013.01); *A61L 2/26* (2013.01); *A61L 2202/11* (2013.01); *A61L 2202/14* (2013.01); *A61L 2202/16* (2013.01); *A61L 2202/26* (2013.01)

(58) Field of Classification Search
CPC ..... A61L 2/10; A61L 2/24; A61L 2/26; A61L 2202/11; A61L 2202/14; A61L 2202/16; A61L 2202/26
See application file for complete search history.

(56) References Cited

U.S. PATENT DOCUMENTS

2007/0200072 A1*  8/2007  Shin .......................... A61L 2/10
                                                           250/455.11

* cited by examiner

*Primary Examiner* — Nicole M Ippolito
*Assistant Examiner* — Hanway Chang
(74) *Attorney, Agent, or Firm* — Barry Choobin; Patent 360

(57) ABSTRACT

Disclosed is a portable sterilization case for personal protective equipment and small articles, such as a mobile phone. The portable sterilization case includes a box body having an opening and inner volume for receiving the articles. The portable sterilization case further includes a cover coupled to the box body forming an enclosed case. The cover is coupled through a hinge joint allowing the cover to pivot in an open position and close position. The inner sides of each the box body and the cover can have an integrated ultraviolet (UV) lamp having a UV-C spectrum configuration. The portable sterilization case further includes a lock member for securing the cover to the box body. In one case, the lock member can be a magnet/magnet pair or magnet/iron pair.

18 Claims, 4 Drawing Sheets

PORTABLE STERILIZATION CASE FOR PERSONAL PROTECTIVE EQUIPMENT

CROSS-REFERENCE TO RELATED APPLICATIONS

This application claims priority from a U.S. provisional patent application with Ser. No. 62/994,041 filed Mar. 24, 2020, both of which are incorporated herein by reference in its entirety.

FIELD OF INVENTION

The present disclosure relates to the field of sterilization using UV-irradiation, and more particularly, the present invention relates to a portable sterilization case for disinfecting a protective personal equipment kit.

BACKGROUND

Sterilization refers to processes that removes, kills, or deactivates microbes from an article. Sterilization can be achieved by a number of processes such as UV-irradiation, chemical irradiation, ozone sterilization, autoclaving, and like processes.

Personal protective equipment (PPE) refers to a specialized suit for protecting healthcare workers from getting infected. The specialized suit provides overall protection against the cross-transmission of pathogenic microorganisms. The suit generally includes a mask, gloves, and gown. Additionally, a PPE kit can also include a face shield/protection, goggles, head cover, and rubber boots. A PPE kit is generally used by health care workers to minimize the chances of getting infected by the patients.

Thus, there is a long-standing need for a portable apparatus that can be used to sterilize the PPE as and when needed.

SUMMARY OF THE INVENTION

The principal object of the present invention is therefore directed a sterilization case of personal protective equipment (PPE).

It is another object of the present invention that the sterilization case is portable.

It is a further object of the present invention that the sterilization case is powered by an integrated battery.

It is another object of the present invention that the sterilization case also provides for charging a mobile phone.

It is an additional object of the present invention that small articles can also be sterilized.

It is a further objective of the present invention that the sterilization case is economical to manufacture.

In one implementation, disclosed is a portable sterilization case for personal protective equipment and small articles, such as a mobile phone. The disclosed portable sterilization case includes a box body having an opening and inner volume for receiving the articles. The portable sterilization case further includes a cover coupled to the box body forming an enclosed case. The cover is coupled through a hinge joint allowing the cover to pivot in an open position and close position. The inner sides of each the box body and the cover can have an integrated ultraviolet (UV) lamp having a UV-C spectrum configuration. The portable sterilization case further includes a lock member for securing the cover to the box body. In one case, the lock member can be a magnet/magnet pair or magnet/iron pair.

In one aspect, the disclosed portable sterilization case can further include one or more charging ports for charging batteries of electronic devices, such as a mobile phone. The one or more charging ports can be integrated into a wall of the box body. In one case, the one or more charging ports can be configured on the outer side of the portable sterilization case. In one case, the one or more charging ports can be configured in the interior of the portable sterilization case. In one case, the charging ports can be configured both inside and outside the portable sterilization case.

In one aspect, the disclosed portable sterilization case can be powered by a portable battery, such as a rechargeable lithium-ion battery. The battery can be integrated into the portable sterilization case. The portable sterilization case can further include a charge status indicator.

In one aspect, the disclosed portable sterilization case includes a sensor, timing circuitry, and a control unit. The sensor configured to detect open and closed states of the cover of the portable sterilization case. The timing circuitry turns the power on to the UV lamps for a predefined duration. The Control Unit can operably connect with the sensor and the timing circuitry.

BRIEF DESCRIPTION OF THE DRAWINGS

The accompanying figures, which are incorporated herein, form part of the specification and illustrate embodiments of the present invention. Together with the description, the figures further explain the principles of the present invention and to enable a person skilled in the relevant arts to make and use the invention.

DETAILED DESCRIPTION

Figure 1:
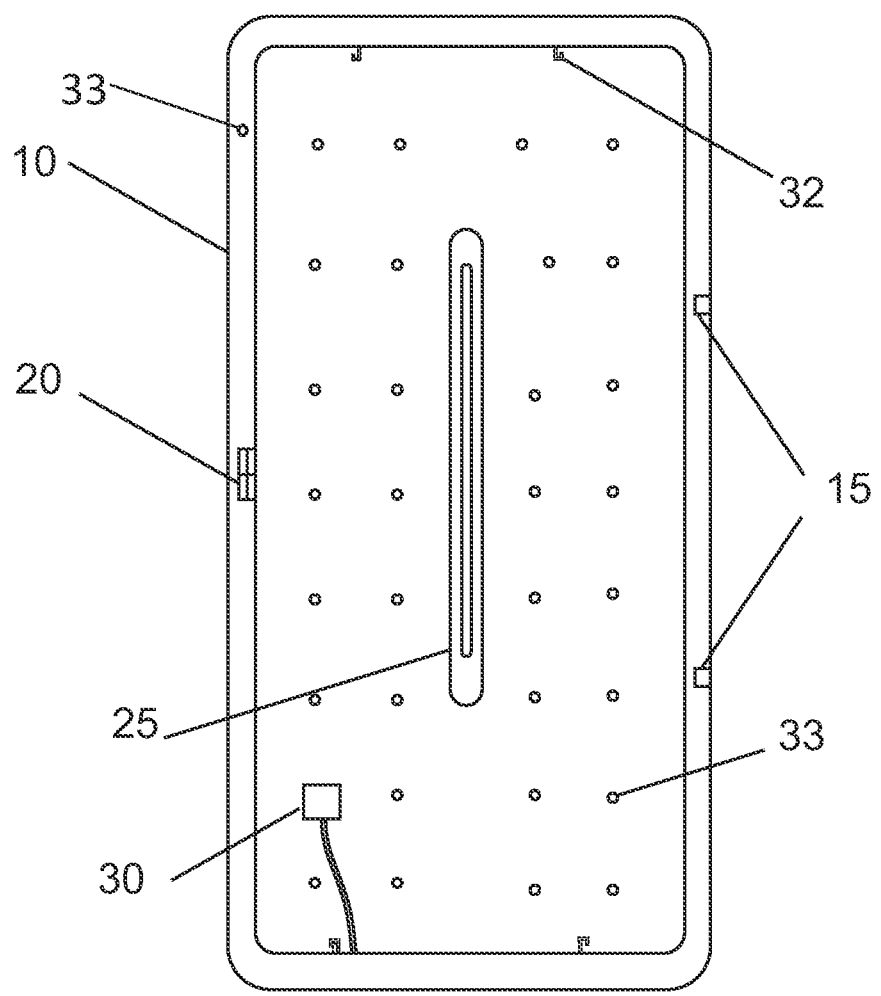
FIG. 1 is a top view of a box body of the sterilization case, according to an exemplary embodiment of the present invention.

Subject matter will now be described more fully hereinafter. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as apparatuses and methods of use thereof. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention, since the scope of the invention will be best defined by the allowed claims of any resulting patent.

The following detailed description is described with reference to the drawings, wherein like reference numerals are used to refer to like elements throughout. In the following description, for purposes of explanation, specific details may be set forth in order to provide a thorough understanding of the subject innovation. It may be evident, however, that the claimed subject matter may be practiced without these specific details. In other instances, well-known structures and devices are shown in block diagram form to facilitate describing the subject innovation. Moreover, the drawings may not be to a scale.

Disclosed is a portable sterilization case of PPE (Personal Protective Equipment) with a rechargeable battery. Referring to FIG. 1 which shows a box body 10 of the disclosed portable sterilization case. The box body 10 is of a container configuration having an opening and an inner volume. The opening can receive an article for sterilization, wherein the size of the article can be proportional to the inner volume of the box body 10. Particularly the box body can have a volume to accommodate a PPE kit for sterilization. Small articles, such as N95 masks, paper currency, coins, gloves, phones, or any personal items can also be sterilized in the disclosed portable sterilization case. The box body 10 includes a base, a front wall, a rear wall, and opposite sidewalls defining the volume of the box body 10. The top of the box body is open to receive an article for sterilization. On an edge of the rear wall can be a fastener 15, such as hinge joints for attaching a cover (shown in FIG. 2). On an edge of the front side can be a locking member 20 for securing the cover to the box body. In one case, the locking member can be a magnet.

Figure 5:
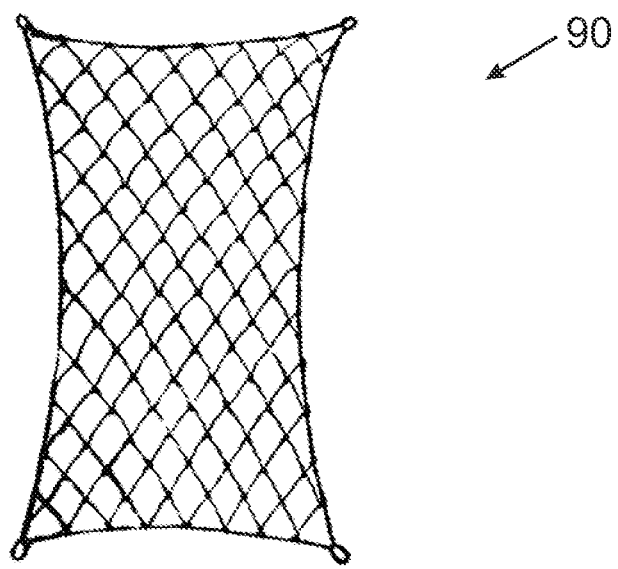
FIG. 5 shows an exemplary embodiment of the net for the sterilization case.

Furthermore, shown in FIG. 1 is an elongated UV-C lamp 25 integrated into the base of the box body 10. The UV-C lamp can be configured to provide irradiation in the UV-C range of spectrum having the desired intensity. The construction and working of the UV-C lamps are known in the art. In one case, the UV-lamp can be a solid-state UV lamp. The inner surface of the box body can be made from a reflective material to enhance the efficiency of UV sterilization. The box body can also be provided with hooks 32 for coupling a net. FIG. 1 shows four hooks 32 coupled on the opposite sidewalls of the box body 10, the four hooks can attach the four loops of the net. An exemplary embodiment of the net is shown in FIG. 5. The net 90 is shown to have loops at four corners that can engage with the four hooks shown in FIG. 1. FIG. 1 also shows several spikes 33 configured on the base of the box body 10. The spikes 33 and the net 90 can enhance the efficiency and effectiveness of the sterilization.

Additionally, the box body 10 can include a charging port 30 for charging of portable electronic device, such as a smartphone, wherein the portable electronic device is secured inside the case 10. The charging port 30 as shown in FIG. 1 extends through a flexible cable, wherein a plug of the charging port 30 can be easily connected to the smart phone. In one implementation, the case body can also be provided with wireless charging option. Any electronic device having wireless charging option can be charged both inside and on top of the sterilization case. For example, the sterilization case can be configured with a QI Wireless charging circuitry for wireless charging.

Figure 2:
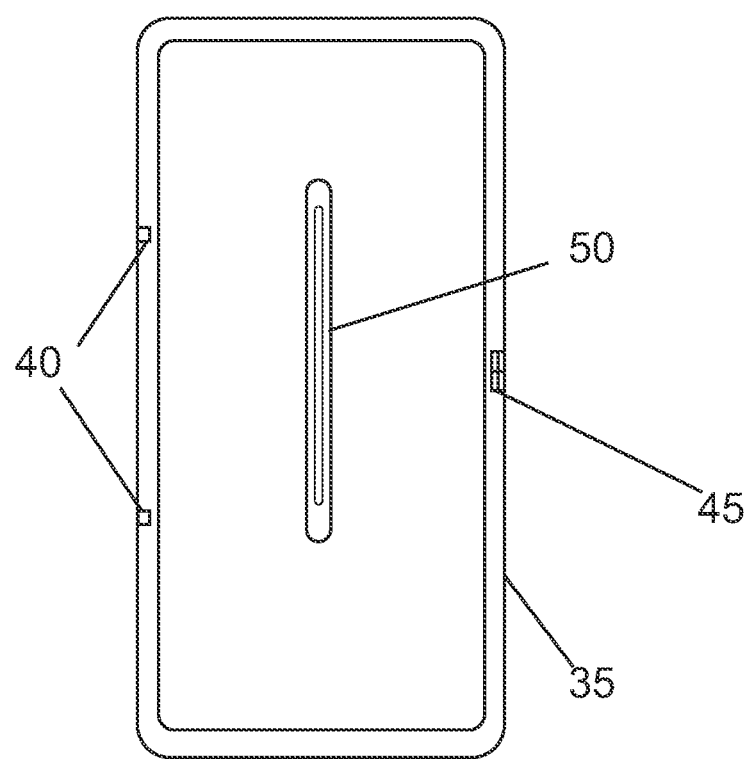
FIG. 2 is a cover of the sterilization case, according to an exemplary embodiment of the present invention.

FIG. 2 shows an embodiment of the cover 35 that can be coupled with the box body 10 for closing its opening. The cover 35 can include fasteners 40 that correspond to the fastener 15 for coupling the cover to the box body 10. In one case the fasteners 15 and 40 can be a pair of hinge joints for pivotally coupling the cover to the box body. The cover can pivot between a closed position and an open position. In the closed position, the opening of the box body is closed by the cover. While in the open position, the inner volume of the box body is accessible. The cover also comprises a locking member 45 that engages with the locking member 20 of the box body for securing the cover to the box body. In one exemplary embodiment, the locking member can be a magnet/magnet or magnet/iron pair that releasably attaches the cover to the box body.

Figure 3:
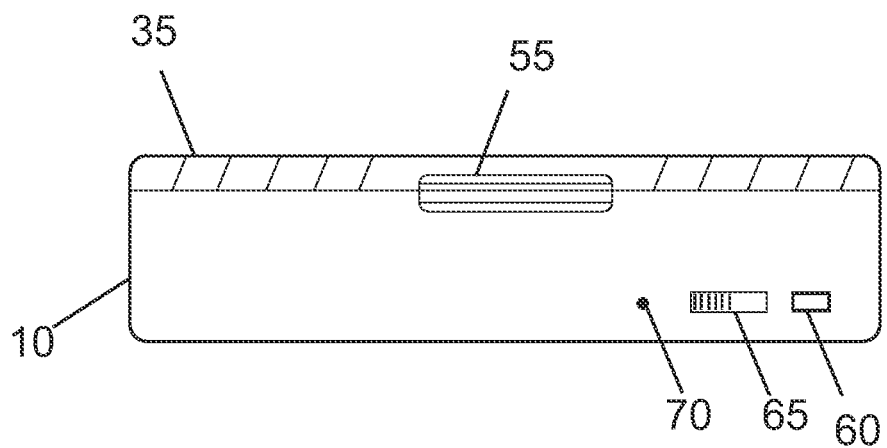
FIG. 3 is a front side of the sterilization case, according to an exemplary embodiment of the present invention.
Figure 4:
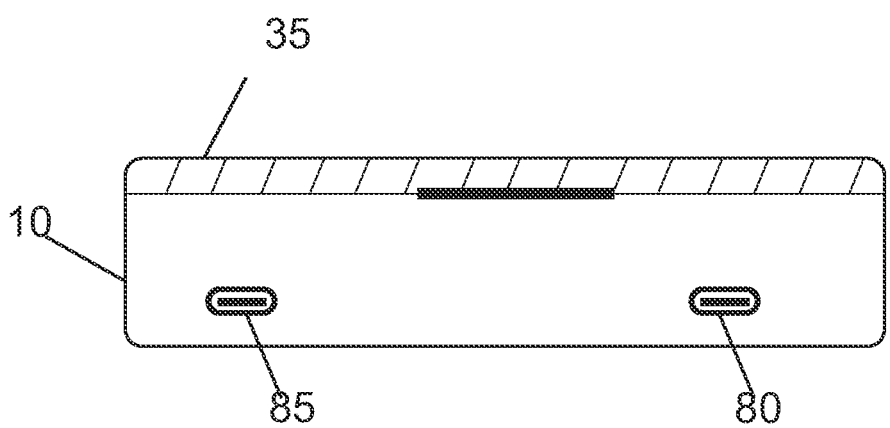
FIG. 4 is a rear view of the sterilization case, according to an exemplary embodiment of the present invention.

The cover can also include a UV-lamp 50 like the UV-lamp of the box body. Both the UV lamps 25 and 50 can simultaneously operate to provide efficient sterilization. The inner surface of the cover can also be made of reflective material for synergizing the UV-sterilization. Referring to FIG. 3, which shows the front side of the disclosed portable sterilization case. The front side of the portable sterilization case can be provided with a recess 55 to lift the cover. The recess can be a protrusion, or a handle coupled to the cover. In one case, the recess can include a locking mechanism as well for securing the cover to the box body. FIG. 3 also shows a button 60 for turning on deep cycle sterilization. The button 60 can trigger a predetermined program defining the intensity of the UV irradiation and the duration. A battery status indicator 65 can show the battery status as well as indicate the charging of the battery. The indicator 70 can show the status of UV lamps. The indicator 70 is off when the UV lamps are off. The indicator 70 can blink showing warming of the UV lamps. A continuous blue indicator can show the normal operation of the UV lamp. While the red indicator can show the deep cycle operation of the UV lamps. FIG. 4 also shows a pair of charging port for charging an electronic device, such as a smartphone. Charging port 80 can be a USB-C type charging port or like known to a skilled person for charging any electronic device. Another charging port 85 can be a USB-C type charging port for wireless charging.

Figure 6:
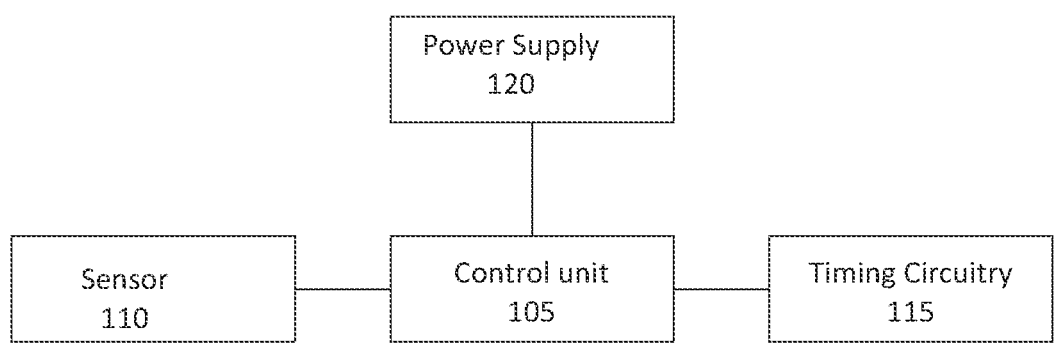
FIG. 6 is a block diagram showing the control unit, sensor, timing circuitry, and a power supply, according to an exemplary embodiment of the present invention.

FIG. 6 shows a control unit 105 operably coupled with a sensor 110, a timing circuitry 115, and a power supply 120. The control unit 105, the sensor 110, the timing circuitry 115, and the power supply 120 can be configured in the case box and the cover of the disclosed portable sterilization case. The sensor can detect the state of the cover i.e. if the cover is in a close state or the open state. The timing circuitry can be configured with a duration for which the UV-lamps should be turned on i.e. the duration of the sterilization cycle. When the cover is closed i.e. switched to the closed state, the event of the closing of the cover can be detected by the sensor and the corresponding signal can be received by the control unit from the sensor. The control unit in response can trigger the timing circuitry which turns the power on to the UV lamps for the predetermined duration. After the predetermined duration, the UV-lamps can be turned off. Moreover, an event of the opening of the cover during the sterilization cycle can trigger the turning of power off to the UV lamps for safety. In one case, the sensor 110 can be a toggle button that can detect the status of the cover. FIG. 1 shows the button 33 on the edge of the box body, such as when the cover is closed, the button is pushed down by the cover. Thus, the button can detect closing and opening of the cover. The opening of the cover, releases the pressure on the button and the button is released, indicating the open state of the cover.

The disclosed portable sterilization case can be powered by a portable rechargeable battery that can also be housed in the box body or cover. The charging ports of the disclosed portable sterilization case can be powered by the rechargeable battery or any other external power supply. In one case, the charging ports and the wireless charging can be powered by a separate external supply. In an alternate case, the rechargeable battery of the disclosed sterilization case can power the 01 wireless charging circuitry and one or more charging ports.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. A portable sterilization case comprising:
   a box body having a base, a front wall, a rear wall, and opposite sidewalls defining an inner volume of the box body, top is open;
   a cover coupled to the box body, the cover configured to switch between an open state and a closed state, in the open state the inner volume is accessible, in the closed state the opening is closed;
   at least one UV lamp configured on an inner surface of the base; and
   a locking member for releasably securing the cover to the box body.

2. The portable sterilization case according to claim 1, wherein the portable sterilization case further comprises a second UV lamp configured on an inner side of the cover.

3. The portable sterilization case according to claim 2, wherein the at least one UV lamp and the second UV lamp are configured to provide irradiation in the UV-C region.

4. The portable sterilization case according to claim 2, wherein the portable sterilization case further comprises:
   a sensor configured to detect the open state and the close state of the cover;
   a control unit operably coupled to the sensor;
   a timing circuitry operably coupled to the control unit, the at least one UV lamp, and the second lamp,
   wherein the control unit is configured to:
      receive a signal from the sensor, the signal indicative of an event of the switching of the cover from the open state to the close state;
      upon receiving the signal, trigger the timing circuitry, wherein the timing circuitry turns the power on to the at least one UV lamp and the second lamp.

5. The portable sterilization case according to claim 1, wherein the portable sterilization case further comprises a plurality of spikes configured on an inner surface of the base.

6. The portable sterilization case according to claim 1, wherein the portable sterilization case further comprises a plurality of hooks coupled to the front wall and the rear wall of the box body.

7. The portable sterilization case according to claim 1, wherein the portable sterilization case further comprises a plurality of hooks coupled to the opposite sidewalls of the box body.

8. The portable sterilization case according to claim 7, wherein the portable sterilization case further comprises a net hooked to the plurality of hooks.

9. The portable sterilization case according to claim 8, wherein the portable sterilization case is having four hooks, the net having four loops secured to the four hooks.

10. The portable sterilization case according to claim 1, wherein the cover is coupled to the box body using a pair of hinge joints.

11. The portable sterilization case according to claim 1, wherein the portable sterilization case further comprises an integrated rechargeable battery.

12. The portable sterilization case according to claim 1, wherein the portable sterilization case further comprises a sensor configured to detect the open state and the close state of the cover.

13. The portable sterilization case according to claim 12, wherein the portable sterilization case further comprises:
   a control unit operably coupled to the sensor;
   a timing circuitry operably coupled to the control unit and the at least one UV lamp,
   wherein the control unit is configured to:
      receive a signal from the sensor, the signal indicative of an event of the switching of the cover from the open state to the close state;
      upon receiving the signal, trigger the timing circuitry, wherein the timing circuitry turns the power on to the at least one UV lamp.

14. The portable sterilization case according to claim 13, wherein the control unit is configured to:
   receive a second signal from the sensor, the signal indicative of a second event of the switching of the cover from the close state to the open state;
   upon receiving the second signal, turns the power off to the at least one UV lamp.

15. The portable sterilization case according to claim 13, wherein the power is turned on by the timing circuitry for a predetermined duration.

16. The portable sterilization case according to claim 1, wherein the locking member is a magnet/magnet pair.

17. The portable sterilization case according to claim 1, wherein the locking member is a magnet/iron pair.

18. The portable sterilization case according to claim 1, wherein the portable sterilization case further comprises a plurality of charging ports configured for charging an electronic device.

* * * * *